United States Patent
Palestrant

[19]

[11] Patent Number: 5,807,311
[45] Date of Patent: Sep. 15, 1998

[54] DIALYSIS CATHETER HAVING RIGID AND COLLAPSIBLE LUMENS AND RELATED METHOD

[76] Inventor: Aubrey M. Palestrant, 6800 N. 47th St., Paradise Valley, Ariz. 85253

[21] Appl. No.: 758,382

[22] Filed: Nov. 29, 1996

[51] Int. Cl.⁶ .................................................. A61M 1/00
[52] U.S. Cl. ................................ 604/28; 604/43; 604/280
[58] Field of Search ................................. 604/27, 35, 43, 604/264, 280, 29, 28

[56] References Cited

U.S. PATENT DOCUMENTS

| | | | |
|---|---|---|---|
| Re. 31,873 | 4/1985 | Howes | 128/674 |
| 4,134,402 | 1/1979 | Mahurkar | 128/214 R |
| 4,385,631 | 5/1983 | Uthmann | 604/284 |
| 4,405,313 | 9/1983 | Sisley et al. | 604/43 |
| 4,406,656 | 9/1983 | Hattler et al. | 604/280 |
| 4,451,252 | 5/1984 | Martin | 604/43 |
| 4,543,087 | 9/1985 | Sommercorn et al. | 604/43 |
| 4,643,711 | 2/1987 | Bates | 604/43 |
| 4,808,155 | 2/1989 | Mahurkar | 604/43 |
| 4,995,865 | 2/1991 | Gahara et al. | 604/43 |
| 5,066,285 | 11/1991 | Hillstead | 604/164 |
| 5,106,368 | 4/1992 | Uldall et al. | 604/43 |
| 5,176,659 | 1/1993 | Mancini | 604/280 |
| 5,472,418 | 12/1995 | Palestrant | 604/43 |

OTHER PUBLICATIONS

"Subclavian Double Lumen Hemodialysis Sets and Trays" Cook Critical Care.

*Primary Examiner*—Corrine M. McDermott
*Attorney, Agent, or Firm*—Cahill, Sutton & Thomas, P.L.C.

[57] ABSTRACT

A multiple-lumen catheter includes a first generally-cylindrical flexible lumen extending between a first distal end and a second proximal end; the first lumen is sufficiently rigid to maintain its generally-cylindrical shape when negative pressure is applied thereto for aspirating fluid from the blood vessel. A second flexible lumen also extends between a first distal end and a second proximal end alongside the first lumen. The first distal end of the second lumen is sufficiently pliable to collapse and flatten in the absence of any positive fluid pressure applied to the second lumen; upon the application of a positive fluid pressure to the second lumen, the collapsible first, distal end of the second lumen expands and assumes a generally-cylindrical shape for introducing fluid into the blood vessel. The first collapsible end of the second lumen can extend beyond the first non-collapsible end of the first lumen for introducing fluid into the blood vessel through the second lumen at a point spaced apart from the first end of the first lumen. In hemodialysis applications, the first lumen is used to aspirate blood, and the second lumen is used to return cleansed blood.

18 Claims, 3 Drawing Sheets

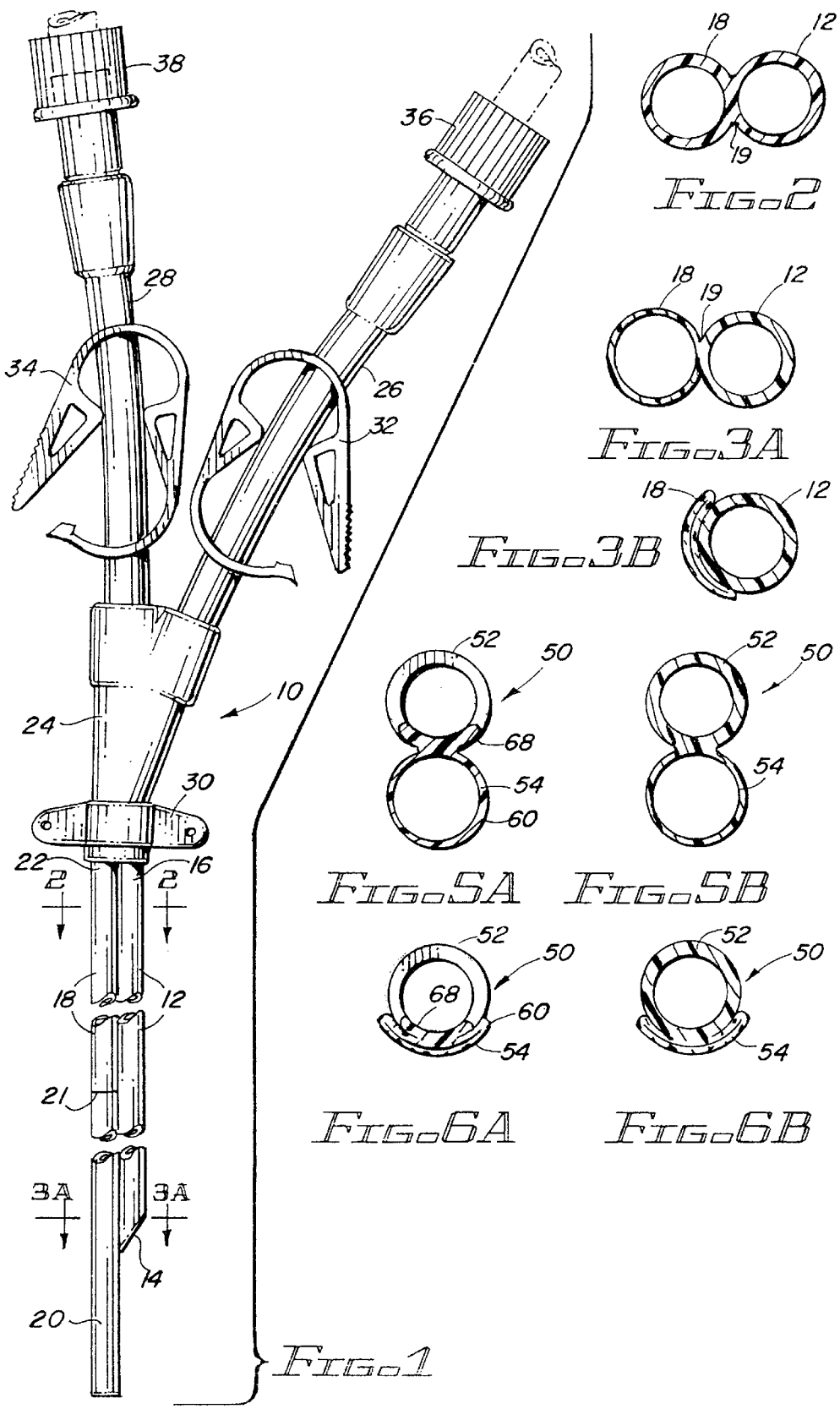

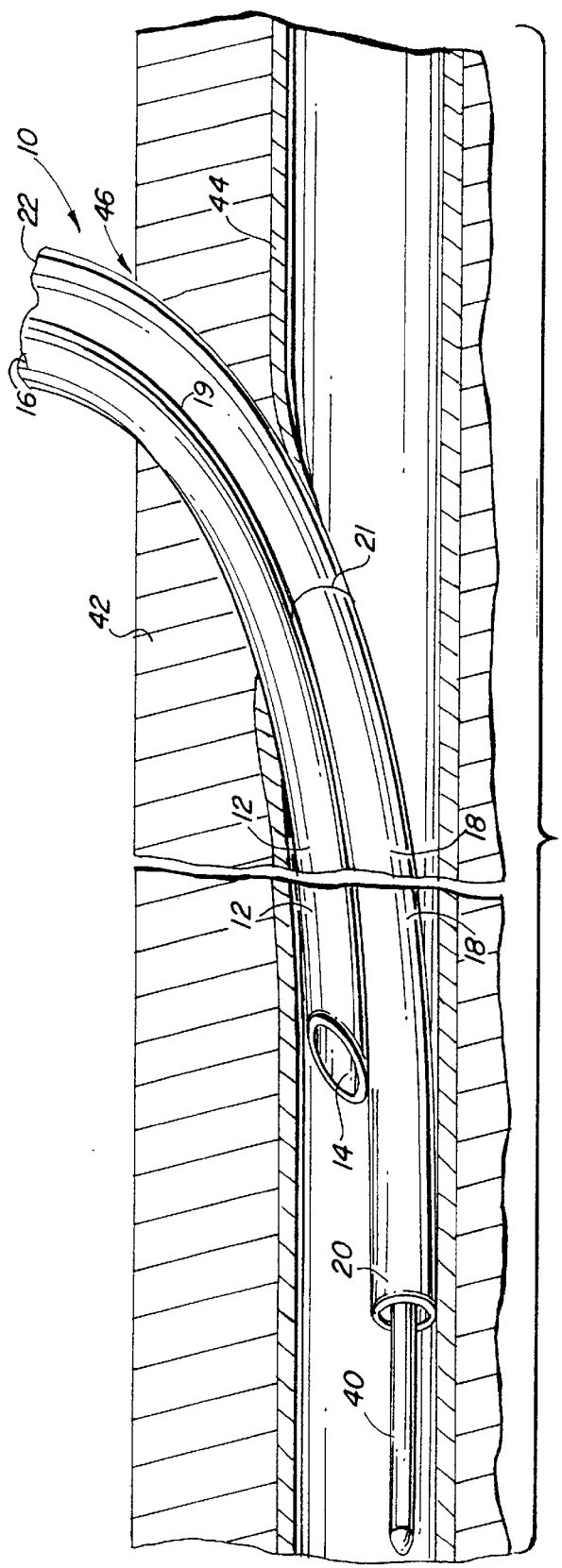
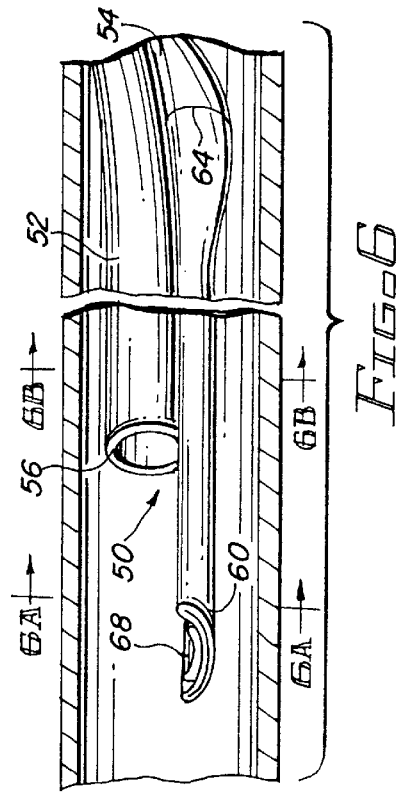
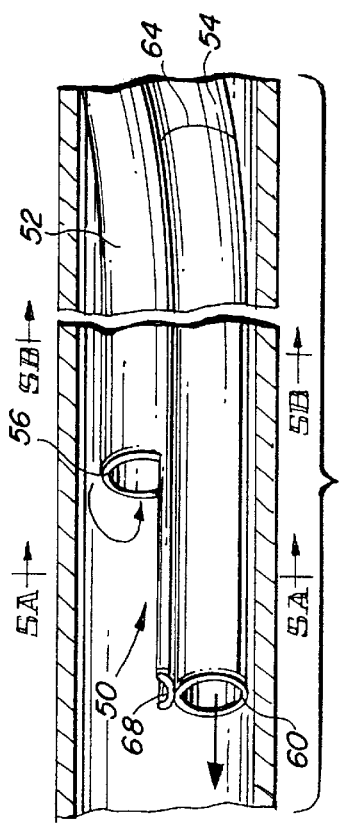

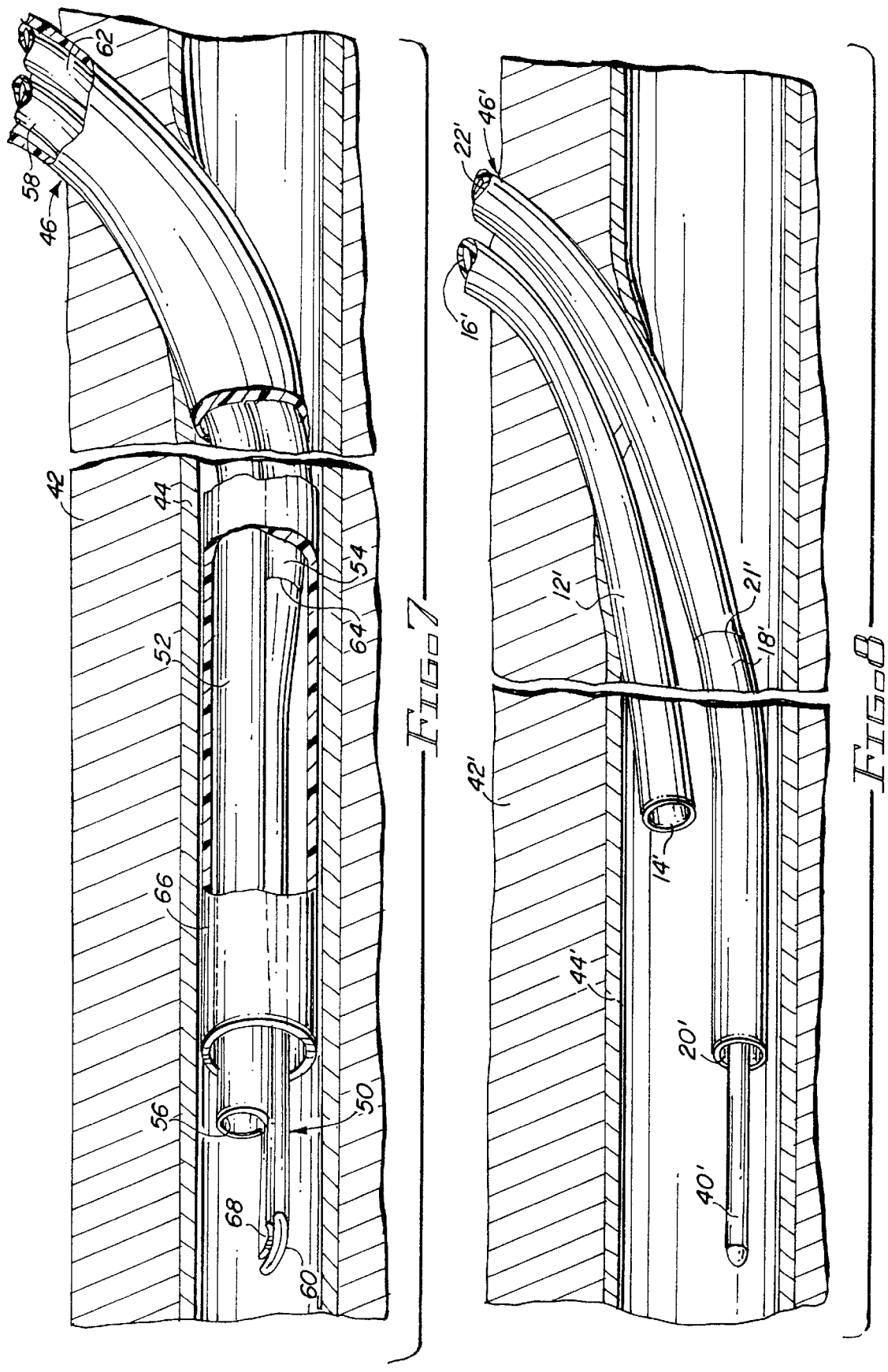

DIALYSIS CATHETER HAVING RIGID AND COLLAPSIBLE LUMENS AND RELATED METHOD

BACKGROUND OF THE INVENTION

1. Field of the Invention

The present invention relates generally to multi-lumen catheters inserted into the vascular system for extended periods of time,-and more particularly, to a semi-collapsible dialysis catheter inserted into the venous system of humans and animals.

2. Description of the Related Art

Placement of large, multi-lumen catheters into humans and animals for various purposes is a commonly performed procedure. In particular, dual-lumen catheters are often placed into the venous system to perform hemodialysis for patients suffering kidney failure. Hemodialysis catheters are designed to accommodate substantial blood flow rates, and are therefore relatively large, often measuring greater than 13 French in size. The cross-sectional profile of such catheters typically have either a twin-circular, "figure-eight" configuration joined at one point, or a so-called double-D configuration. In both of these designs, the lumens of the blood inlet and blood outflow channels are both equal in size, thereby balancing the blood removal flow rate with the blood return flow rate. However, the necessity to make both lumens equal in size creates an overall catheter of relatively large cross-sectional dimensions. Such large profile catheters can cause complications when left in the venous system.

Placement of a catheter within a blood vessel necessarily creates turbulence, and a slowing of blood flow, within the blood vessel. Generally, the greater the cross-sectional area of the catheter relative to the blood vessel, the greater the induced turbulence and slowing of the blood in the vessel. In addition, the catheter is a foreign body, and the surface of the catheter in contact with blood acts as a nidus for clot formation. These factors are leading causes of vein clotting, resulting in occlusion of the vein and irreversible damage. Permanent obstruction of the vein prevents blood flow, which may ultimately cause debilitating swelling of the limb being drained by these veins. Another danger of such clots is that they can break away and flow through the bloodstream to the heart and lungs, causing obstruction to the vascular system and severe complications.

A further problem with the existing dual-lumen catheters is that blood may remain in the catheter during rest periods when the catheter is not being used to perform dialysis; blood collected within the lumens may form a clot, obstructing the passage of fluids through the catheter, thereby rendering the catheter unusable. Should this occur, the catheter may need to be removed and replaced with a new one. This procedure poses an inconvenience and a burden to both the patient and the attending physician, and adds to the cost of maintaining venous access for dialysis.

U.S. Pat. No. 5,106,368 to Uldall et al. discloses a dual-lumen catheter for vascular access. The distal portion of the catheter includes two tubular members attached to each other, one of which is formed by a thinner wall to make such tubular member collapsible. The collapsible lumen is temporarily held in its collapsed state by a peel-away sheath for insertion into the blood vessel. Once the catheter is in position, the sheath is removed and the collapsed tubular member regains its circular configuration. Thus, Uldall et al. do not reduce the cross-sectional area or surface area of the catheter once it is placed in the vein. In addition, once such catheter is placed in the vein, blood can enter, and remain within, both lumens of the catheter in the absence of fluid flow. Apparently recognizing the likelihood of clotting, Uldall et al. teach that the thicker-walled, negative pressure blood suction lumen should be made longer than the thinner-walled, positive pressure blood return lumen to reduce the accumulation of blood clots and resulting blockages. Uldall et al. concede that such design increases blood recirculation between the two lumens, but state that such increase in recirculation is minimal.

U.S. Pat. No. 4,406,656 issued to Hattler, et al., discloses a multi-lumen catheter adapted to be inserted through the center of an insertion needle into the vein of a patient. The catheter disclosed by Hattler et al. includes two or more collapsible, elastic peripheral lumens formed around a flexible, but non-collapsible, central lumen. The peripheral lumens stretch to accommodate increasing flow and, therefore, a greater pressure must be applied to the infused fluid in order to adequately stretch the lumen to open it. The need to generate such additional pressure to fully inflate one or more peripheral lumens is a disadvantage, since the equipment being used to infuse fluids into the blood vessel must then be capable of generating such greater pressures. Moreover, all of the lumens shown by Hattler et al. terminate at the same distal point; therefore, the catheter design disclosed by Hattler et al. can not prevent mixing of two infused medications, nor can it prevent recirculation of infused fluids with aspirated fluids.

In addition, the '656 patent to Hattler et al. teaches persons skilled in the art to extend the collapsible, peripheral lumens through the entry point of the patient's skin and vein. In this regard, Hattler et al. state that the patient's skin is resilient enough to accommodate the expansion of the collapsed lumens during fluid flow without tearing the skin. However, when significant fluid flow rates are required, as during hemodialysis, the degree of expansion of a collapsed lumen is great enough to effectively increase the size of the puncture at the skin entry site and the vein, posing the risk of tearing, bleeding, and infection.

Accordingly, it is an object of the present invention to provide a multi-lumen catheter which reduces the likelihood of formation of clots within the blood vessel into which the catheter is placed.

It is another object of the present invention to provide such a catheter which decreases its cross-sectional dimensions within the blood vessel when the catheter is not being used for infusion or dialysis, while providing a satisfactory flow path to infused fluids during infusion or dialysis procedures.

Still another object of the present invention is to provide such a catheter which minimizes the surface area of the catheter exposed to the blood when infusion or dialysis procedures are not being performed.

A further object of the present invention is to provide such a catheter which minimizes the likelihood of blood entering, or collecting within, an infusion lumen of the catheter and forming a blockage therein.

A still further object of the present invention is to provide a method for gaining access to a blood vessel to perform chronic dialysis while minimizing the risks of creating blood clots around or within the catheter.

A yet further object of the present invention is to provide a method of conveniently placing such a catheter within the desired blood vessel using commonly available vascular apparatus.

Still another object of the present invention is to provide such a catheter and method which maintains a relatively constant catheter tract size through the skin entry point and blood vessel wall whether fluid is being infused or not being infused.

These and other objects of the present invention will become more apparent to those skilled in the art as the description thereof proceeds.

SUMMARY OF THE INVENTION

Briefly described, and in accordance with the preferred embodiments disclosed herein, the present invention relates to a multiple lumen catheter for placement into a blood vessel of a patient and including a first flexible lumen having a generally-cylindrical shape extending between opposing first and second ends. This first lumen, while being flexible, is sufficiently rigid to maintain its generally-cylindrical shape, and resist a collapse, even when negative pressure is applied thereto, as when aspirating fluid from the blood vessel through the first lumen. The multiple lumen catheter also includes a second flexible lumen secured to the first lumen and extending generally parallel to the first flexible lumen thereto between opposing first and second ends. Unlike the first lumen, the first end of the second lumen is sufficiently pliable to collapse and flatten in the absence of any positive fluid pressure applied to the second lumen; on the other hand, when a positive fluid pressure is applied to the second end of the second lumen, it is sufficiently pliable to expand and assume a generally-cylindrical shape for introducing fluid into the blood vessel.

The first ends of both the first and second lumens are adapted to extend within the blood vessel of the patient generally proximate to one another, while the second ends of the first and second lumens remain outside the patient's body for exchanging fluids with the blood vessel of the patient. The second end of the second lumen, which is disposed outside the patient's body, is sufficiently rigid to maintain a generally-cylindrical shape in the absence of any positive fluid pressure applied to the second end of the second lumen. The second lumen includes a transition region which separates the collapsible first end thereof from the remaining non-collapsible portion of the second lumen; following insertion of the catheter, the transition region extends within the blood vessel of the patient.

The catheter described above can be advantageously used to perform hemodialysis. In such instance, the first end of the second lumen extends beyond the first end of the first lumen; in this manner, fluid introduced through the second lumen enters the blood vessel at a point spaced apart from the first end of the first lumen. The first non-collapsible lumen serves as a blood inlet lumen, and the second end of such first lumen is coupled to an aspiration port of a hemodialysis machine to withdraw blood containing toxins from the blood vessel. The second lumen serves as a blood return lumen, and the second end of the second lumen is coupled to a cleaned blood return port of the hemodialysis machine for returning cleaned blood back to the blood vessel.

To aid in the coupling of the second ends of the first and second lumens to a dialysis machine or other equipment, the catheter may include first and second connector tubes, as well as a connector hub. The connector hub is secured to the second ends of the first and second lumens and couples the second ends of the first and second lumens to respective ones of the connector tubes.

The catheter of the present invention can be inserted into a blood vessel using an introducer sheath, with or without the aid of a guide wire. The introducer sheath, which is preferably of the "peel-away" type, extends through the patient's skin and into the patient's blood vessel, and the first ends of the first and second lumens are inserted into and through the introducer sheath for placement within the blood vessel.

Assuming that no guide wire is to be used, then the portion of the first end of the second lumen which extends beyond the first end of the first lumen should be reinforced to prevent the first end of said second lumen from buckling during insertion of the multiple lumen catheter into the blood vessel. Placement of the catheter can be facilitated if the first and second lumens of the catheter are secured to each other, although the attachment of the first and second lumens to each other is not essential in order to practice the present invention. The tubular wall that forms the first lumen is preferably extruded from a thermoplastic material, and the portion of such tubular wall that adjoins the second lumen can be extruded beyond the first end of the first lumen to extend to the first end of the second lumen to provide the desired reinforcement to the first end of the second lumen.

If a guide wire is used to assist in placing the catheter, the guide wire is first placed into the blood vessel through the skin of the patient. Once again, a peel-away type introducer sheath is preferably placed over the guide wire and into the blood vessel to form a smooth passage for the catheter. The collapsible first end of the second lumen is threaded over the proximal end of the guide wire, and the first ends of the first and second lumens are then guided through the introducer sheath into the blood vessel over the guide wire. The guide wire temporarily stiffens the collapsible first end of the second lumen and prevents it from buckling during insertion. To reduce the likelihood of trauma to the blood vessel during insertion without an introducer sheath, the first end of the first lumen can be tapered somewhat.

The present invention also relates to a method for exchanging fluids with a blood vessel of a patient, wherein such method includes the step of providing a first flexible lumen having a generally-cylindrical shape and having opposing first and second ends. The method includes the step of maintaining the first lumen sufficiently rigid to hold its generally-cylindrical shape when negative pressure is applied to the second end of the first lumen to aspirate fluid from the blood vessel. The method of the present invention also includes the step of providing a second flexible lumen having opposing first and second ends, and extending the second lumen generally parallel to the first flexible lumen. The method further includes the step of forming the first end of the second lumen to be sufficiently pliable to collapse and flatten in the absence of any positive fluid pressure applied to the second end of the second lumen, while allowing the first end of the second lumen to expand and assume a generally-cylindrical shape upon the application of a positive fluid pressure to the second end of the second lumen, as when introducing fluid into the blood vessel.

The second end of the second lumen is formed to be sufficiently rigid to maintain a generally-cylindrical shape in the absence of any positive fluid pressure applied thereto. The first ends of the first and second lumens are inserted through the patient's skin and into a blood vessel, while leaving the second ends of the first and second lumens outside the patient's body in order to access the first and second lumens externally. The method of the present invention includes the step of forming a transition region within the second lumen separating the collapsible first end of the second lumen from the remaining non-collapsible portion of the second lumen; the first ends of the first and second lumens are inserted sufficiently far into the blood vessel to include the transition region of the second lumen within the blood vessel.

One aspect of the above-described method is to perform hemodialysis by coupling the second end of the first lumen to an aspiration port of a hemodialysis machine to withdraw blood containing toxins from the blood vessel, and coupling the second end of the second lumen to a cleaned blood return port of the hemodialysis machine for returning cleaned blood to the blood vessel. In practicing this aspect of the present invention, the first end of the second lumen is preferably extended beyond the first end of the first lumen for introducing clean blood into the blood vessel through the second lumen at a point spaced apart from the first end of the first lumen.

The method of the present invention may include the step of securing a portion of the outer periphery of the first lumen to an adjoining portion of the outer periphery of the second lumen. The step of providing the first lumen can advantageously include the step of extruding generally-cylindrical walls that form the first lumen; in this event, the extruding step may advantageously include the step of extruding a portion of the wall of the first lumen that is secured to the second lumen beyond the first end of the first lumen to the first end of the second lumen to reinforce the first end of the second lumen and thereby prevent the first end of the second lumen from buckling during insertion into the blood vessel. The method of the present invention may also include the step of placing an introducer sheath, preferably of the peel-away type, through the patient's skin and into the patient's blood vessel, and thereafter inserting the first ends of the first and second lumens through the introducer sheath. The introducer sheath may then be peeled away, leaving the catheter in place within the blood vessel.

Another aspect of the method of the present invention contemplates the placement of the first and second lumens into the blood vessel with the aid of a guide wire. In this regard, the method may include placing a guide wire through the patient's skin and into the patient's blood vessel, and thereafter inserting the first end of the second lumen over the guide wire and advancing the first ends of the first and second lumens through the patient's skin and into the blood vessel. This method may also include the further step of tapering the first end of the first lumen to reduce the likelihood of trauma to the blood vessel when the second lumen is advanced over the guide wire.

BRIEF DESCRIPTION OF THE DRAWINGS

FIG. 1 is a top view of a dual lumen catheter in accordance with one of the preferred embodiments of the present invention.

FIG. 2 is a cross-sectional view taken through first and second lumens of the catheter of FIG. 1 proximate the connector hub, as indicated by lines 2—2 in FIG. 1.

FIG. 3A is a cross-sectional view through the first and second lumens of the catheter of FIG. 1 proximate the first ends of such lumens, as indicated by lines 3A—3A in FIG. 1, when fluid is being infused through a collapsible lumen.

FIG. 3B is a cross-sectional view similar to that shown in FIG. 3A, but showing the second lumen flattened and collapsed against the first lumen when no fluid is being infused through the second lumen.

FIG. 4 is a sectional view of the distal portion of the catheter shown in FIG. 1 during insertion into a blood vessel over a guide wire.

FIG. 5 is a sectional view through a patient's blood vessel illustrating the distal tip of a second embodiment of the present invention, wherein a portion of the non-collapsible first lumen is extended to reinforce the collapsible end of the second lumen, and wherein the first lumen aspirates blood while the second lumen returns cleaned blood in a hemodialysis application.

FIG. 5A is a sectional view of the distal tip shown in FIG. 5 taken through lines 5A-5A as indicated in FIG. 5 during a hemodialysis procedure.

FIG. 5B is a sectional view similar to that shown in FIG. 5A but taken through lines 5B—5B as indicated in FIG. 5.

FIG. 6 is a perspective view of the distal tip of the catheter shown in FIG. 5 after the hemodialysis function has been terminated, wherein the longer second lumen has assumed its collapsed state.

FIG. 6A is a sectional view of the distal tip of the catheter shown in FIG. 6 taken through lines 6A—6A following termination of the hemodialysis procedure.

FIG. 6B is a sectional view similar to that shown in FIG. 6A but taken through lines 6B—6B following termination of the hemodialysis procedure.

FIG. 7 is a sectional view of the dual lumen catheter shown in FIGS. 5 and 6 being placed into a patient's blood vessel through a peel-away introducer sheath.

FIG. 8 illustrates an alternate embodiment of the present invention similar to that shown in FIG. 4, but wherein the first and second lumens are not secured to one another.

DETAILED DESCRIPTION OF THE PREFERRED EMBODIMENTS

A multiple lumen catheter constructed in accordance with one preferred embodiment of the present invention is shown in FIGS. 1–4 and is identified generally by reference numeral 10. As will be explained in greater detail in conjunction with FIG. 4, catheter 10 is designed to be placed into a blood vessel of a patient. Catheter 10 includes a first flexible tubular lumen 12 which, as shown best in FIGS. 2, 3A and 3B, has a generally-cylindrical shape. As used herein, the term "generally-cylindrical" is intended to include circular cross-sections as well as oval and elliptical cross-sections. First lumen 12 is preferably formed of a thermoplastic material that can be extruded.

As indicated in FIG. 1, first lumen 12 extends between a first distal end 14 and an opposing second proximal end 16. As shown in FIG. 4, first end 14 of first lumen 12 is adapted to extend within a blood vessel 44 of a patient, while second end 16 of first lumen 12 is adapted to remain outside the patient's body for exchanging fluids with blood vessel 44.

As indicated in FIGS. 2, 3A, and 3B, first lumen 12 is formed by a tubular wall that has a relatively constant thickness along its length. First lumen 12 is sufficiently rigid to maintain its generally-cylindrical shape under normal usage, including those instances when a negative pressure is applied to second end 16 of first lumen 12, as when aspirating blood from blood vessel 44. On the other hand, first lumen 12 is sufficiently flexible to avoid discomfort or trauma to the patient.

Catheter 10 also includes a second flexible tubular lumen 18 extending generally parallel to first flexible lumen 12. As shown in FIGS. 1–4, second lumen 18 is secured alongside first lumen 12; however, as indicated by the alternate embodiment illustrated in FIG. 8, the first and second lumens needs not be physically secured to each other along their respective lengths. Within FIGS. 1–4, the contact point at which the outer periphery of first lumen 12 is joined to the outer periphery of second lumen 18 is indicated by reference numeral 19. Second lumen 18 may be formed of the same thermoplastic material as first lumen 12, and first lumen 12 and second lumen 18 can be extruded concurrently, if desired.

Second lumen 18 extends between a first distal end 20 and a second opposing end 22. As shown in FIG. 4, first distal end 20 of second lumen 18 is adapted to extend within blood vessel 44 generally proximate first end 14 of first lumen 12. As shown in FIG. 4, second end 22 of second lumen 18 is adapted to remain outside the patient's body for exchanging fluids with blood vessel 44.

As indicated by the cross-sectional drawing of FIG. 2, the second end 22 of second lumen 18 is formed by a tubular wall that has a thickness comparable to that of first lumen 12. Thus, second end 22 of second lumen 18 is sufficiently rigid to maintain a generally-cylindrical shape even in the absence of any positive fluid pressure applied thereto. In contrast, as shown in the cross-sectional drawing of FIG. 3A, the first distal end 20 of second lumen 18 is formed by a tubular wall of much thinner construction. First distal end 20 of second lumen 18 is sufficiently pliable to collapse and flatten in the absence of any positive fluid pressure applied to second end 22 of second lumen 18, as is indicated in FIG. 3B. It its collapsed state shown in FIG. 3B, second lumen 18 has a smaller surface area exposed to blood, and catheter 10 occupies a smaller cross-sectional area within the blood vessel. On the other hand, first distal end 20 of second lumen 18 is also sufficiently pliable to expand and assume a generally-cylindrical shape upon the application of a positive fluid pressure to second end 22 of second lumen 18, as when introducing blood or another fluid into blood vessel 44. In the preferred embodiment of the present invention, first end 20 of second lumen 18 is formed of a collapsible, but relatively inelastic, material; accordingly, when first end 20 is infusing fluid into blood vessel 44, first end 20 expands to a generally-cylindrical shape of a fixed diameter. However, the term "pliable", as used herein, should not be construed as being limited to inelastic materials.

Within FIGS. 1 and 4, reference numeral 21 indicates the transition point at which second lumen 18 transitions from a semi-rigid non-collapsible tubular structure to a yielding and collapsible tubular structure. Thus, transition point 21 separates the collapsible first end 20 of second lumen 18 from the remaining non-collapsible portion of second lumen 18. As indicated within FIG. 4, catheter 10 is inserted sufficiently far into blood vessel 44 to assure that transition point 21 lies within the blood vessel. In this manner, one may assure that the catheter tract 46 formed through the skin 42 and blood vessel 44 does not significantly change in size when collapsible end 20 of second lumen 18 is expanded by infused fluid. Therefore, the risk of skin tearing, bleeding and/or infection is minimized while maintaining the benefit of a collapsible lumen within the blood vessel.

As indicated in FIG. 1, second ends 16 and 22 of first and second lumens 12 and 18 are preferably secured to a Y-hub, or connector hub, 24. Extending from such connector hub are a first connector tube 26 and a second connector tube 28. Connector hub 24 couples first connector tube 26 to second end 16 of first lumen 12 for communicating therewith, while coupling second connector tube 28 to the second end 22 of second lumen 18 for communicating therewith. As shown in FIG. 1, a suture wing 30 may be rotatably secured to connector hub 24 for allowing the connector hub to be sutured to the patient's skin adjacent the puncture site 46 (see FIG. 4). In addition, a pair of clamps 32 and 34 may be secured over connector tubes 26 and 28, respectively, for selectively closing off such connector tubes before and after each hemodialysis procedure. A pair of luer lock connector fittings 36 and 38 are secured to the free ends of connector tubes 26 and 28, respectively, for conveniently allowing catheter 10 to be interconnected with fluid infusion lines, aspiration lines, or with the blood inlet and blood return ports of a hemodialysis machine. In the latter case, second end 16 of first lumen 12 is coupled, via connector tube 26 and luer lock fitting 36, to an aspiration port of a hemodialysis machine to withdraw blood containing toxins from the blood vessel; second end 22 of second lumen 18 is coupled, via connector tube 28 and luer lock fitting 38, to a cleaned blood return port of the hemodialysis machine to return cleaned blood to the blood vessel.

While FIGS. 2, 3A and 3B illustrate that the first distal end 20 of second lumen 18 is thinner than the second end 22 thereof, the most important distinction is that first distal end 20 is more pliable and collapsible as compared with second end 22. Using the same material, but of different thicknesses, is but one way to achieve such objective. It is also possible to use different materials to form first distal end 20 and second end 22; in this event, transition point 21 may represent a junction point at which a first tube made of a first pliable material, and extending from transition point 21 to the distal end of lumen 18, is joined to a second tube made of a second flexible, but non-collapsible, material extending from transition point 21 to connector hub 24.

As illustrated in FIGS. 1 and 4, first distal end 20 of second lumen 18 lies generally close to, but is spaced apart from, first distal end 14 of first lumen 12. Moreover, first distal end 20 of second lumen 18 extends beyond first end 14 of first lumen 12; in this manner, blood or other fluid introduced into blood vessel 44 through second lumen 18 enters such blood vessel at a point spaced apart from first end 14 of first lumen 12. In a hemodialysis application, this spacing helps to prevent mixing of cleaned return blood through first end 20 of second lumen 18 with blood being aspirated from the blood vessel through first end 14 of first lumen 12.

FIG. 4 illustrates one manner by which catheter 10 may be placed within a blood vessel. As indicated in FIG. 4, a distal end of a guide wire 40 is first inserted into blood vessel 44 through catheter tract 46, as by advancing guide wire 40 through a hollow needle. Catheter 10 is then placed into blood vessel 44 by threading first collapsible end 20 of second lumen 18 over the proximal end of guide wire 40 and advancing both first end 20 of second lumen 18 and first end 14 of first lumen 12 through the catheter tract 46 in the patient's skin 42 and into blood vessel 44. Guide wire 40 helps rigidify collapsible end 20 of second lumen 18, and prevents collapsible end 20 from buckling during insertion. As indicated in FIGS. 1 and 4, the first end 14 of first lumen may be tapered to more easily part through the skin 42 and blood vessel wall 44 to reduce the likelihood of trauma to the blood vessel when said second lumen is guided over the guide wire.

A second embodiment of the present invention is illustrated in FIGS. 5–7. As will be explained in greater detail herein, this second embodiment is adapted to be placed within a blood vessel through a peel-away introducer sheath without the aid of a guide wire. Within FIG. 7, dual lumen catheter 50 includes a first flexible, but non-collapsible, lumen 52 and a second flexible lumen 54 extending generally parallel to lumen 52 and secured thereto along its length. First lumen 52 has a generally-cylindrical shape and extends between opposing first and second ends 56 and 58, respectively. As indicated in FIGS. 5–7, first end 56 of first lumen 52 is adapted to extend within blood vessel 44, while second end 58 is adapted to remain outside the patient's body for exchanging fluids with blood vessel 44. As in the case of the first embodiment of the present invention, first lumen 52 is sufficiently rigid to maintain its generally-cylindrical shape even when negative pressure is applied to second end 58 thereof, as when aspirating fluid through first lumen 52.

Second flexible lumen 54 extends between opposing first and second ends 60 and 62, respectively. First end 60 of second lumen 54 is adapted to extend within blood vessel 44 generally proximate first end 56 of first lumen 52, while second end 62 of second lumen 54 is adapted to remain outside the patient's body for exchanging fluids with blood vessel 44. As in the case of the first embodiment described above, first end 60 of second lumen 54 is sufficiently pliable to collapse and flatten against first lumen 52 in the absence of any positive fluid pressure applied to second end 62 of second lumen 54, as illustrated in FIGS. 6 and 7; on the other hand, first end 60 of second lumen 54 is sufficiently pliable to expand and assume a generally cylindrical shape upon the application of a positive fluid pressure to second end 62 of second lumen 54 when introducing fluid into blood vessel 44, as shown in FIG. 5. As in the case of the first embodiment described above, second lumen 54 includes a transition region, designated by reference numeral 64 in FIGS. 5–7, which separates the collapsible first end 60 of second lumen 54 from the remaining non-collapsible portion thereof. As further indicated in FIGS. 5–7, this transition region 64 is adapted to extend within blood vessel 44, such that the non-collapsible portion of second lumen 54 extends through the puncture site 46 of the patient's skin 42.

Within the second embodiment of the present invention shown in FIGS. 5–7, the first end 60 of second lumen 54 again extends beyond first end 56 of first lumen 52 to facilitate the introduction of fluid from second lumen 54 into blood vessel 44 at a point spaced apart from first end 56 of first lumen 52. As explained above, this spatial relationship has advantages when using such dual lumen catheter to perform hemodialysis. In other applications, the relationship of the lengths of first lumen 52 and second lumen 54 could be reversed, or perhaps both lumens could be of the same length. When hemodialysis is to be performed, second end 58 of first lumen 52 is coupled to an aspiration port of a hemodialysis machine to withdraw blood containing toxins from blood vessel 44; second end 62 of second lumen 54 is coupled to a cleaned blood return port of the hemodialysis machine to return cleaned blood to blood vessel 44. While not shown in FIGS. 5–7, those skilled in the art will appreciate that first and second connector tubes and a connector hub, similar to those identified by reference numerals 24, 26, and 28 in FIG. 1, are preferably secured to second ends 58 and 62 of first and second lumens 52 and 54, respectively, to facilitate the interconnection of catheter 50 to aspiration/infusion ports.

Within FIG. 7, a peel-away type introducer sheath 66 is shown to facilitate the placement of catheter 50 into blood vessel 44. As indicated in FIG. 7, introducer sheath 66 is inserted through the patient's skin 42 at catheter tract 46 and into the patient's blood vessel 44, in a manner well known to those skilled in the art. Following placement of introducer sheath 66, first ends 56 and 60 of catheter 50 are inserted into the proximal end of introducer sheath 66, and catheter 50 is then advanced through introducer sheath 66 sufficiently far to ensure that transition region 64 lies within blood vessel 44. Introducer sheath 66 is then pulled apart and peeled away, leaving catheter 50 in place.

In the second embodiment of the present invention illustrated in FIGS. 5–7, it is desirable to reinforce the collapsible first end 60 of second lumen 54 to prevent that portion of first end 60 which extends beyond first end 56 from folding over and/or buckling during placement. It will be recalled that guide wire 40 (see FIG. 4) provided such reinforcement in the case of the first embodiment of the present invention. On the other hand, first end 60 of second lumen 54 should remain sufficiently collapsible to substantially flatten between infusion procedures.

Assuming that first lumen 52 is formed by an extruded tubular wall, then the desired reinforcement for first end 60 of second lumen 54 can be provided by simply continuing the extrusion of a portion of such tubular wall beyond first end 56 of first lumen 52. As shown in FIGS. 5 and 7, an arcuate segment 68 of the tubular wall forming first lumen 52 extends beyond first end 56 thereof until reaching first end 60 of second lumen 54. This arcuate segment corresponds to the portion of first lumen 52 that adjoins, and is secured to, the outer periphery of second lumen 54. As indicated in FIGS. 5A and 6A, this extended arcuate segment 68 can be thicker, and more rigid, than first end 60 of second lumen 54, thereby serving as an elongated reinforcing member and providing the desired reinforcement for preventing first end 60 from buckling during placement. During manufacture, the tubular wall forming first lumen 52 can initially be extruded to be of the same length as second lumen 54, after which all of the material forming such tubular wall, with the exception of arcuate segment 68, is removed between first end 60 and first end 56.

Alternatively, the elongated reinforcing member for preventing the first end 60 of second lumen 54 from buckling could, if desired, be incorporated within an arcuate portion of the tubular wall forming first end 60 itself. For example, in cross-section, an arcuate (e.g., 40°) of the tubular wall of first end 60 could be more rigid than the remaining arcuate portions (320°) of such tubular wall for allowing first end 60 to substantially flatten and collapse when no fluid is being infused, while nonetheless preventing first end 60 from buckling during placement into the blood vessel through an introducer sheath.

FIG. 8 illustrates a third embodiment of the present invention which is similar to the first embodiment shown in FIGS. 1–4, except that the first and second lumens are not secured along their length to each other. Those features illustrated in FIG. 8 which correspond to features shown in FIGS. 1–4 are designated by correspondingly primed reference numerals. Since, in the case of this third embodiment, first lumen 12' is not secured to second lumen 18', a guide wire 40' is used during placement to reinforce the collapsible end 20' of second lumen 18'. In addition, it is advisable to also use an introducer sheath, like that shown as 66 in FIG. 7, to facilitate placement of such catheter within the blood vessel. While this third embodiment may not form as compact a structure, when infusion is stopped, as compared with catheter 10 of FIG. 4 or catheter 50 of FIG. 7, the collapsible portion of second lumen 18' nonetheless will collapse against either first lumen 12', or against the walls of blood vessel 44', thereby reducing the overall dimensions of the catheter when not in use.

The descriptions of the preferred embodiments of the present invention set forth above also demonstrate a preferred method of exchanging fluids with a blood vessel of a patient. This preferred method includes the step of providing a first flexible lumen, such as lumen 12, having a generally-cylindrical shape and having opposing first and second ends 14 and 16. The preferred method also includes the step of ensuring that the first lumen 12 is sufficiently rigid to maintain its generally-cylindrical shape when negative pressure is applied to the second end 16 thereof.

The preferred method also includes the step of providing a second flexible lumen, such as lumen 18, having opposing first and second ends 20 and 22, and extending generally parallel to first flexible lumen 12. In practicing the preferred method, the first end 20 of the second lumen 18 is formed to be sufficiently pliable to collapse and flatten in the absence of any positive fluid pressure applied to the second end 22 of the second lumen 18; on the other hand, first end 20 is formed to be sufficiently pliable to expand and assume a generally-cylindrical shape upon the application of a positive fluid pressure to second end 22 of second lumen 18 when introducing fluid into the blood vessel. The preferred method includes the step of forming second end 22 of second lumen 18 to be sufficiently rigid and non-collapsible to maintain a generally cylindrical shape even in the absence of any pressurized fluid applied to second lumen 18.

The preferred method of exchanging fluids with a blood vessel of a patient further includes the step of inserting the first ends 14 and 20 of the first and second lumens 12 and 18, respectively, through the patient's skin 42 and into the blood vessel 44, while leaving the second ends 16 and 22 of the first and second lumens 12 and 18, respectively, outside the patient's body in order to access the first and second lumens externally. In forming the second lumen 18, a transition region 21 is created therein which separates the collapsible first end 20 of second lumen 18 from the remaining non-collapsible portion thereof. The preferred method also includes the step of inserting the first ends 14 and 20 of first and second lumens 12 and 18 sufficiently far into the blood vessel 44 to include the transition region 21 of second lumen 18 within blood vessel 44.

Those skilled in the art will now appreciate that an improved multiple lumen catheter has been described which reduces the likelihood of formation of clots within a blood vessel into which the catheter is placed by allowing at least one of such lumens to collapse between infusion procedures. The ability of such lumen to collapse within the blood vessel decreases its cross-sectional dimensions within the blood vessel when the catheter is not being used for infusion or dialysis, but without compromising the size of the flow path when the collapsible lumen is expanded to infuse fluids. Such decrease in cross-section dimension causes less turbulence and slowing of blood which minimizes the likelihood of vessel thrombosis. In its collapsed state, the collapsible lumen minimizes the overall surface area of the catheter exposed to the blood when infusion or dialysis procedures are not being performed, thereby decreasing the risk of blood clot formation on the surface of the catheter. In addition, when the collapsible lumen is in its collapsed state, the likelihood that blood will enter or collect within the collapsed lumen of the catheter is reduced, thereby lessening the risk that a blockage will form within such lumen, which would require replacement of the catheter. Moreover, by keeping the transition point of the second lumen within the blood vessel, a relatively constant puncture size is maintained through the skin entry point, whether or not fluid is being infused.

While the present invention has been described with respect to several preferred embodiments thereof, such description is for illustrative purposes only, and is not to be construed as limiting the scope of the invention. Various modifications and changes may be made to the described embodiments by those skilled in the art without departing from the true spirit and scope of the invention as defined by the appended claims.

I claim:

1. A method of exchanging fluids with a blood vessel of a patient, said method comprising the steps of:

a. providing a first flexible tube surrounding a first lumen, the first flexible tube having a generally-cylindrical shape and having opposing first and second ends, while ensuring that the first tube is sufficiently rigid to maintain its generally-cylindrical shape when negative pressure is applied to the second end of the first lumen when aspirating fluid from the blood vessel;

b. providing a second flexible tube surrounding a second lumen, the second flexible having opposing first and second ends, and extending generally parallel to the first flexible tube;

c. forming the first end of the second tube to be sufficiently pliable to collapse and flatten in the absence of any positive fluid pressure applied to the second end of the second lumen, and sufficiently pliable to expand and assume a generally-cylindrical shape upon the application of a positive fluid pressure to the second end of said second lumen when introducing fluid into the blood vessel;

d. forming the second end of the second tube to be sufficiently rigid and non-collapsible to maintain a generally-cylindrical shape in the absence of any positive fluid pressure applied to the second end of said second lumen;

e. inserting the first ends of the first and second tubes through the patient's skin and into a blood vessel, while leaving the second ends of the first and second tubes outside the patient's body in order to access the first and second lumens externally;

f. forming a transition region within the second tube separating the collapsible first end of the second tube from the remaining non-collapsible portion of the second tube; and g. inserting the first ends of the first and second tubes sufficiently far into the blood vessel to include the transition region of the second tube within the blood vessel.

2. The method recited by claim 1 including the further step of extending the first end of the second tube beyond the first end of the first tube for introducing fluid into the blood vessel through the second lumen at a point spaced apart from the first end of the first lumen.

3. The method recited by claim 2 further including the steps of coupling the second end of the first lumen to an aspiration port of a hemodialysis machine to withdraw blood containing toxins from the blood vessel, and coupling the second end of the second lumen to a cleaned blood return port of the hemodialysis machine to return cleaned blood to the blood vessel, thereby performing hemodialysis.

4. The method recited by claim 2 further including the step of securing the first tube along its length to the second tube.

5. The method recited by claim 4 wherein the step of providing the first tube includes the step of extruding generally-cylindrical walls that form the first tube, and wherein the extruding step includes the step of extruding a portion of the wall of the first tube that is secured to the second tube beyond the first end of the first lumen to the first end of the second tube to prevent the first end of the second tube from buckling during insertion into the blood vessel.

6. The method recited by claim 1 further including the step of placing an introducer sheath through the patient's skin and into the patient's blood vessel, and thereafter performing said inserting step by inserting the first ends of the first and second tubes through the introducer sheath.

7. The method recited by claim 6 including the step of tapering the first end of the first tube to reduce the likelihood of trauma to the blood vessel when the second lumen is advanced over the guide wire.

8. The method recited by claim 1 including the step of placing a guide wire through the patient's skin and into the patient's blood vessel, and thereafter performing said inserting step by inserting the first end of the second lumen over the guide wire and advancing the first ends of the first and second tubes through the patient's skin and into the blood vessel.

9. A multiple lumen catheter for placement into a blood vessel of a patient, comprising in combination:

a. a first flexible tube having a generally-cylindrical shape and having opposing first and second ends, the first end of said first tube being adapted to extend within the blood vessel of the patient, the second end of said first tube being adapted to remain outside the patient's body for exchanging fluids with the blood vessel of the patient, said first tube being sufficiently rigid to maintain its generally-cylindrical shape when negative pressure is applied to the second end of said first tube to aspirate fluid from the blood vessel, said first tube defining a first lumen;

b. a second flexible tube extending generally parallel to said first flexible tube, said second tube having opposing first and second ends, the first end of said second tube being adapted to extend within the blood vessel of the patient generally proximate the first end of said first tube, the second end of said second tube being adapted to remain outside the patient's body for exchanging fluids with the blood vessel of the patient, the first end of said second tube being sufficiently pliable to collapse and flatten in the absence of any positive fluid pressure applied to the second end of said second tube, and sufficiently pliable to expand and assume a generally-cylindrical shape upon the application of a positive fluid pressure to the second end of said second tube when introducing fluid into the blood vessel, said second tube defining a second lumen;

c. the second end of said second tube being sufficiently rigid and non-collapsible to maintain a generally-cylindrical shape in the absence of any positive fluid pressure applied to the second end of said second tube; and d. said second tube including a transition region separating the collapsible first end of said second tube from the remaining non-collapsible portion of said second tube, wherein said transition region is adapted to extend within the blood vessel of the patient.

10. The multiple lumen catheter recited by claim 9 wherein the first end of said second tube extends beyond the first end of said first tube for introducing fluid into the blood vessel through said second tube at a point spaced apart from the first end of said first tube.

11. The multiple lumen catheter recited by claim 10 wherein said first flexible tube is secured along its length to said second flexible tube.

12. The multiple lumen catheter recited by claim 11 wherein said first tube includes an extruded tubular wall secured to said second tube, and wherein a portion of said extruded tubular wall of said first tube is extruded beyond the first end of said first tube to the first end of said second tube to prevent the first end of said second tube from buckling during insertion of the multiple lumen catheter into the blood vessel.

13. The multiple lumen catheter recited by claim 12 further including an introducer sheath extending through the patient's skin and into the patient's blood vessel, said first and second tubes extending into and through said introducer sheath.

14. The multiple lumen catheter recited by claim 9 wherein the second end of said first tube is adapted to be coupled to an aspiration port of a hemodialysis machine to withdraw blood containing toxins from the blood vessel, and wherein the second end of said second tube is adapted to be coupled to a cleaned blood return port of the hemodialysis machine to return cleaned blood to the blood vessel, whereby the catheter may be used to perform hemodialysis.

15. The multiple lumen catheter recited by claim 9 including first and second connector tubes and further including a connector hub, the connector hub being secured to the second ends of said first and second tubes, the connector hub coupling the second end of said first tube to said first connector tube, and the connector hub coupling the second end of said second tube to said second connector tube.

16. The multiple lumen catheter recited by claim 9 wherein the first end of said second tube includes an elongated reinforcing member to prevent the first end of said second tube from buckling during insertion of the multiple lumen catheter into the blood vessel.

17. The multiple lumen catheter recited by claim 9 including a guide wire extending through said second lumen for inserting the multiple lumen catheter into the blood vessel through the skin of the patient.

18. The multiple lumen catheter recited by claim 17 wherein the first end of said first tube is tapered to reduce the likelihood of trauma to the blood vessel when said second lumen is guided over the guide wire.

* * * * *